US00PP36698P2

(12) United States Plant Patent
Flore

(10) Patent No.: US PP36,698 P2
(45) Date of Patent: May 20, 2025

(54) ***PHALAENOPSIS* PLANT NAMED 'MI02969'**

(50) Latin Name: *Phalaenopsis hybrida*
Varietal Denomination: MI02969

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 18/946,908

(22) Filed: Nov. 13, 2024

Related U.S. Application Data

(60) Provisional application No. 63/548,541, filed on Nov. 14, 2023.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

U.S. PATENT DOCUMENTS

PP32,286 P2 * 10/2020 Van Swieten ..... A01H 5/02
Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'MI02969', characterized by its upright plant habit; relatively compact, semi-erect to arching leaves; strong flowering stems; freely flowering habit with typically about two to three inflorescences per plant, each inflorescence with numerous flowers; orange-colored flowers with purplish red-colored venation; and excellent postproduction longevity.

2 Drawing Sheets

Figure 1:
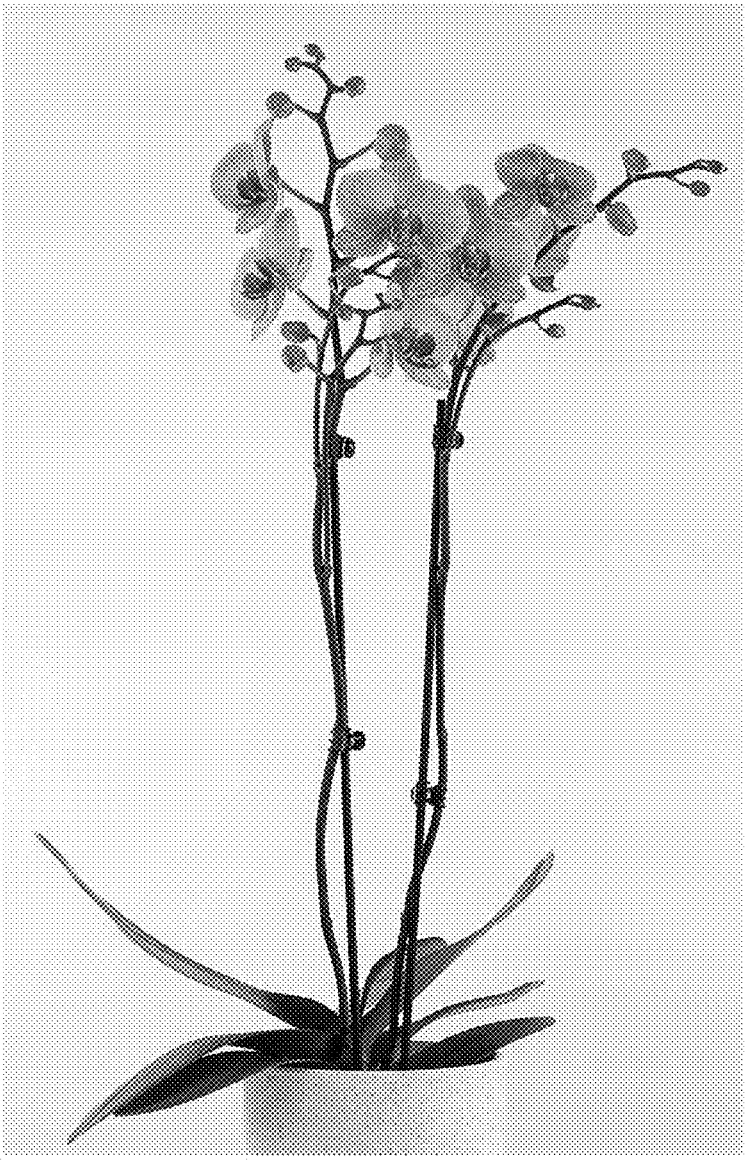

Botanical designation: *Phalaenopsis hybrida.*
Cultivar denomination: 'MI02969'.

REFERENCED TO CLOSELY-RELATED APPLICATIONS

A European Community Plant Breeder's Rights application for the instant plant was filed by the Applicant/Assignee, Microflor N.V. of Lochristi, Belgium on Sep. 6, 2023, application number 2023/1859. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'MI02969'.

The new *Phalaenopsis* plant is a product of a planned breeding program conducted by the Inventor in Lochristi, Belgium. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May, 2017 in Lochristi, Belgium of a proprietary selection of *Phalaenopsis hybrida* identified as code number PH02559, not patented, as the female, or seed, parent with *Phalaenopsis hybrida* 'MI00708', previously identified as code number PH02066, and disclosed in U.S. Plant Pat. No. 30,721, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in February, 2020.

Asexual reproduction of the new *Phalaenopsis* plant by in vitro meristem propagation in a controlled environment in Lochristi, Belgium since March, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02969'. These characteristics in combination distinguish 'MI02969' as a new and distinct *Phalaenopsis* plant:

1. Upright plant habit.
2. Relatively compact, semi-erect to arching leaves.
3. Strong flowering stems.
4. Freely flowering habit with typically about two to three inflorescences per plant, each inflorescence with numerous flowers.
5. Orange-colored flowers with purplish red-colored venation.
6. Excellent postproduction longevity.

Plants of the new *Phalaenopsis* can be compared to plants of the female parent selection. Plants of the new *Phalaen-*

*opsis* differ primarily from plants of the female parent selection in the following characteristics:

1. Plants of the new *Phalaenopsis* are taller than plants of the female parent selection.
2. Plants of the new *Phalaenopsis* flower about two weeks earlier than plants of the female parent selection.
3. Plants of the new *Phalaenopsis* are more freely flowering than plants of the female parent selection.

Plants of the new *Phalaenopsis* can be compared to plants of the male parent, 'MI00708'. Plants of the new *Phalaenopsis* differ primarily from plants of 'MI00708' in the following characteristics:

1. Plants of the new *Phalaenopsis* flower about one week earlier than plants of the female parent selection.
2. Plants of the new *Phalaenopsis* are not as freely flowering as plants of 'MI00708'.
3. Flowers of plants of the new *Phalaenopsis* are orange in color with purplish red-colored venation whereas flowers of plants of 'MI00708' are yellow in color.

Plants of the new *Phalaenopsis* can be compared to plants of *Phalaenopsis hybrida* 'PHALGASCIJ', disclosed in U.S. Plant Pat. No. 32,286. In side-by-side comparisons, plants of the new *Phalaenopsis* differ primarily from plants of 'PHALGASCIJ' in flower color as flowers of plants of the new *Phalaenopsis* are orange in color with purplish red-colored venation whereas flowers of plants of 'PHALGASCIJ' are coppery in color with dark red-colored stripes.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI02969' grown in a container.

Figure 2:
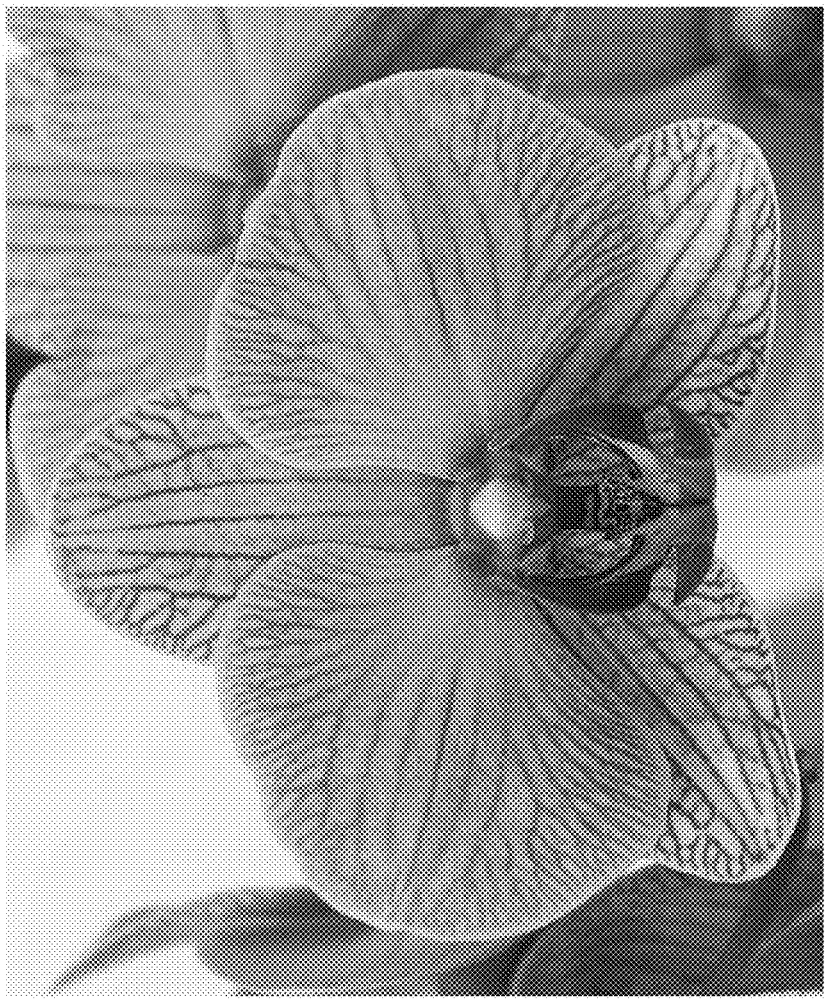

The photograph on the second sheet (FIG. 2) is a close-up view of typical flowers of 'MI02969'.

DETAILED BOTANICAL DESCRIPTION

The aforementioned photographs and following observations and measurements describe plants grown during the late summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were 69 weeks old when the photographs and the detailed description were taken. In the following description, color references are made to The Royal Horticultural Society Colour Chart, 2001 Edition, except where general terms of ordinary dictionary significance are used.

Botanical classification: *Phalaenopsis hybrida* 'MI02969'.

Parentage:

*Female parent*.—Proprietary selection of *Phalaenopsis hybrida* identified as code number PH02559, not patented.

*Male parent*.—*Phalaenopsis hybrida* 'MI00708' (previously identified as code number PH02066), disclosed in U.S. Plant Pat. No. 30,721.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 14.5 cm.

*Plant height, substrate level to top of inflorescences*.—About 53 cm.

*Plant diameter or spread*.—About 39 cm.

Leaf description:

*Arrangement and quantity*.—Distichous, simple; sessile; about seven leaves per plant; leaves are relatively compact.

*Length*.—About 22 cm.

*Width*.—About 9.4 cm.

*Aspect*.—Semi-erect to arching.

*Shape*.—Elliptic.

*Apex*.—Unequal obtuse.

*Base*.—Sheathing.

*Margin*.—Entire.

*Texture and luster, upper and lower surfaces*.—Smooth, glabrous; glossy.

*Venation pattern*.—Camptodromous.

*Color*.—When opening and fully expanded leaves, upper surface: Close to 137A; venation, close to 137A. When opening and fully expanded leaves, lower surface: Close to 138A; venation, close to 138A.

Inflorescence description:

*Appearance and flowering habit*.—Showy zygomorphic flowers arranged on axillary branched racemes; typically two to three inflorescences per plant; each inflorescence with about nine flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period; flowers open about five weeks after flower buds develop.

*Flower longevity*.—Long flowering period and excellent postproduction longevity, individual flowers maintain good substance for about eight weeks on the plant; flowers not persistent.

*Inflorescence length* (*lowermost flower to inflorescence apex*).—About 22 cm.

*Inflorescence width*.—Axially, about 18 cm and radially, about 8 cm.

*Flower buds*.—Height: About 2 cm. Diameter: About 1.3 cm. Shape: Ovate. Color: Close to 151B variably overlain with close to 165A.

*Flower diameter*.—About 8.6 cm.

*Flower depth*.—About 2.8 cm.

*Petals, quantity and arrangement*.—Three, two lateral petals and one center petal transformed into a labellum.

*Lateral petals*.—Length: About 3.9 cm. Width: About 4.6 cm. Shape: Flabellate. Apex: Rounded. Margin: Entire. Texture and luster, upper and lower surfaces: Smooth, glabrous, velvety; matte. Color: When opening, upper surface: Close to 20B overlain with close to 167C; venation, close to 54B. When opening, lower surface: Close to 163C. Fully opened, upper surface: Close to 20C overlain with close to 168D; venation, close to 54B; color does not change with subsequent development. Fully opened, lower surface: Close to 162B; color does not change with subsequent development.

*Labella*.—Appearance: Tri-lobed with two lateral lobes and a central lobe. Central lobe length: About 2 cm. Central lobe width: About 1.8 cm. Shape, lateral lobes: Oblanceolate; apices, obtuse; and margins, entire. Shape, central lobe: Trullate; apices, cleft with short and narrow recurved cirrhose tips; margins, entire. Texture and luster, upper and lower surfaces: Smooth, glabrous, moderately velvety; matte. Callosities: Located at the base of the labellum and attachment point of the lateral petals; about 5 mm in length, about 4 mm in width and about 4 mm in height. Color, central lobe: When opening and fully opened, upper surface: Close to 4A; towards the base, close to 6A. When opening and fully opened, lower surface: Close to 155D; towards the margins, close to 46A and towards the apex, close to 78C. Color, lateral lobes: When opening and fully opened, upper surface: Distally, close to 46A; proximally, close to 69A; at the base, close to 8D with stripes, close to 59A. When opening and fully opened, lower surface: Distally, close to 59A; at the apex, close to 46A; at the base, close to 8D. Color, callosities: Close to 10B with dots, close to 59B.

*Sepals*.—Quantity and arrangement: Three, two lower lateral sepals and one upper dorsal sepal. Length, lateral sepal: About 4.4 cm. Width, lateral sepals: About 2.8 cm. Length, dorsal sepal: About 4.2 cm. Width, dorsal sepal: About 3 cm. Shape, lateral sepals: Ovate. Shape, dorsal sepal: Elliptical. Apex, lateral sepals: Bluntly acute. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 20B overlain with close to 167C; venation, close to 54B. When opening, lower surface: Close to 151D. Fully opened, upper surface: Close to 20C overlain with close to 168D; venation, close to 54B; color does not change with subsequent development. Fully opened, lower surface: Close to 160A; color does not change with subsequent development.

*Peduncles*.—Length: About 60 cm. Diameter, proximally: About 4 mm. Strength: Strong, somewhat flexible. Aspect: Mostly upright. Texture and luster: Smooth, glabrous; matte. Color: Close to 200A.

*Pedicels*.—Length: About 4 cm. Diameter: About 3 mm. Strength: Moderately strong; flexible. Aspect: About 90° from peduncle axis. Texture and luster: Smooth, glabrous; matte. Color: Proximally, close to 200B, and distally, close to 75C.

*Reproductive organs*.—Androecium: Column length: About 7 mm. Column width: About 6 mm. Column color: Close to 75A; distally, close to 155D. Pollinia quantity: Two. Pollinia diameter (per two pollinia): About 2 mm. Pollinia color: Close to 24A. Gynoecium: Stigma length: About 3 mm. Stigma width: About 3 mm. Stigma shape: Reniform. Stigma color: Close to 76D. Ovary length: About 1.5 cm. Ovary diameter: About 2 mm. Ovary color: Close to 75D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 30° C. and to be suitable for USDA Hardiness Zones 10 and higher.

It is claimed:

1. A new and distinct *Phalaenopsis* plant named 'MI02969' as herein illustrated and described.

* * * * *